United States Patent [19]

Higgs et al.

[11] Patent Number: 4,559,811

[45] Date of Patent: Dec. 24, 1985

[54] CONSISTOMETER

[75] Inventors: Kenneth O. Higgs; Jimmy D. Everett, both of Port Neches, Tex.

[73] Assignee: Texaco Inc., White Plains, N.Y.

[21] Appl. No.: 612,505

[22] Filed: May 21, 1984

[51] Int. Cl.[4] .......................................... G01N 11/14
[52] U.S. Cl. ...................................................... 73/59
[58] Field of Search .................................... 73/59, 54

[56] References Cited

U.S. PATENT DOCUMENTS

| 3,812,706 | 5/1974 | Higgs et al. | 73/59 |
|---|---|---|---|
| 4,043,183 | 8/1977 | Higgs et al. | 73/59 |
| 4,044,602 | 8/1977 | Higgs et al. | 73/59 |
| 4,044,603 | 8/1977 | Higgs et al. | 73/59 |
| 4,499,753 | 2/1985 | Carr | 73/59 |

FOREIGN PATENT DOCUMENTS 2058341  4/1981  United Kingdom ................... 73/59

*Primary Examiner*—Stewart J. Levy
*Assistant Examiner*—Joseph W. Roskos
*Attorney, Agent, or Firm*—Robert A. Kulason; James J. O'Loughlin; Ronald G. Gillespie

[57] ABSTRACT

An improved consistometer which continuously measures the consistency of a stream of material from apparatus manufacturing the material includes a resilient blade rotated in the stream of material and which is rotated about an axis that is parallel to the direction of flow of the stream of material. A reference blade is rotated in synchronism with the resilient panel. A pair of detectors are arranged with the blade in the manner so that each detector detects the passage of a corresponding blade and provides a corresponding electrical signal. A circuit connected to the detectors provides a start pulse and a stop pulse in accordance with the signals from the detectors and not to noise. A clock provides timing pulses. A network connected to the start and stop pulse circuit and to the clock determines the consistency of the material in accordance with the start and stop pulses and the timing pulses.

6 Claims, 2 Drawing Figures

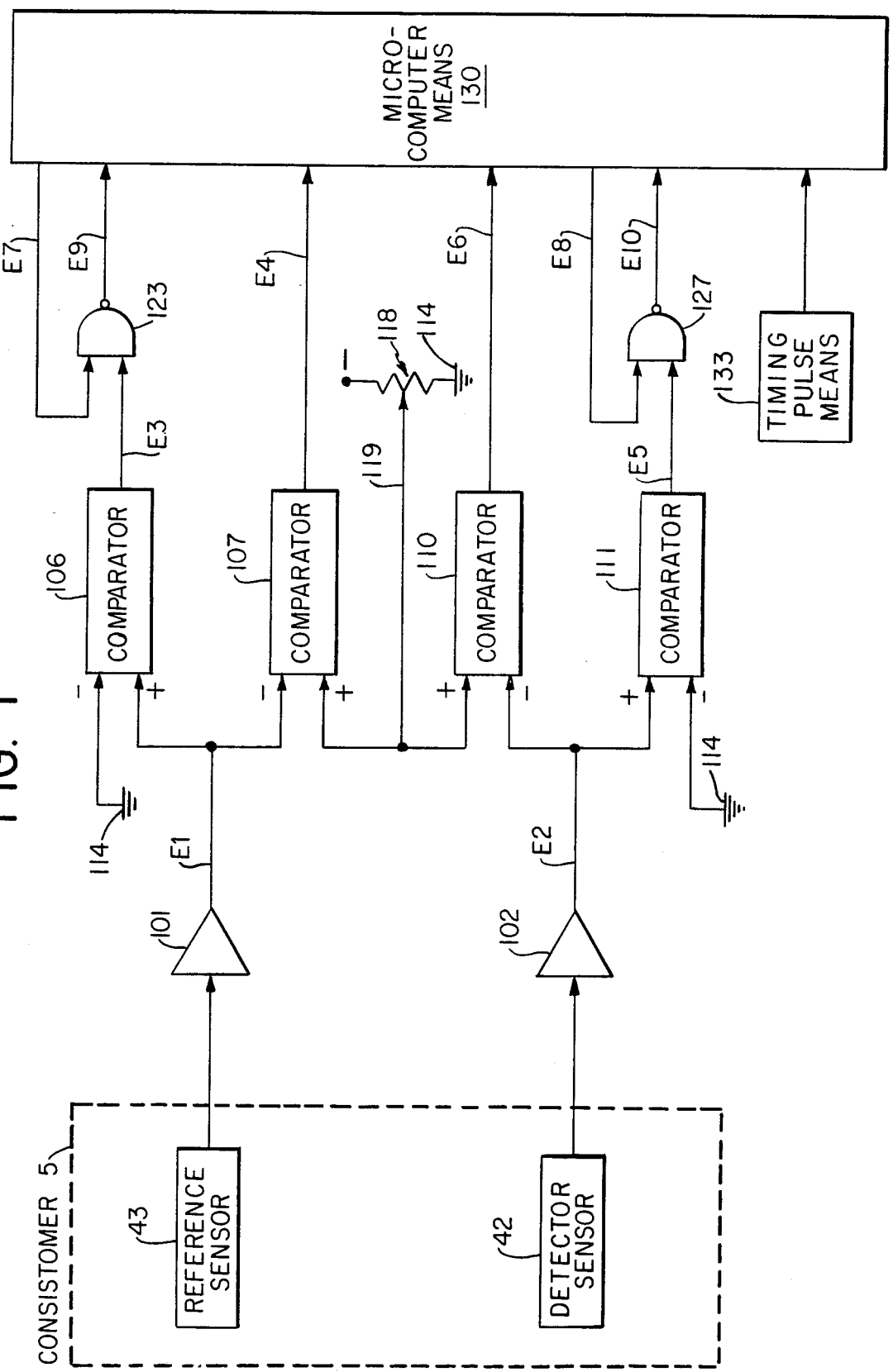

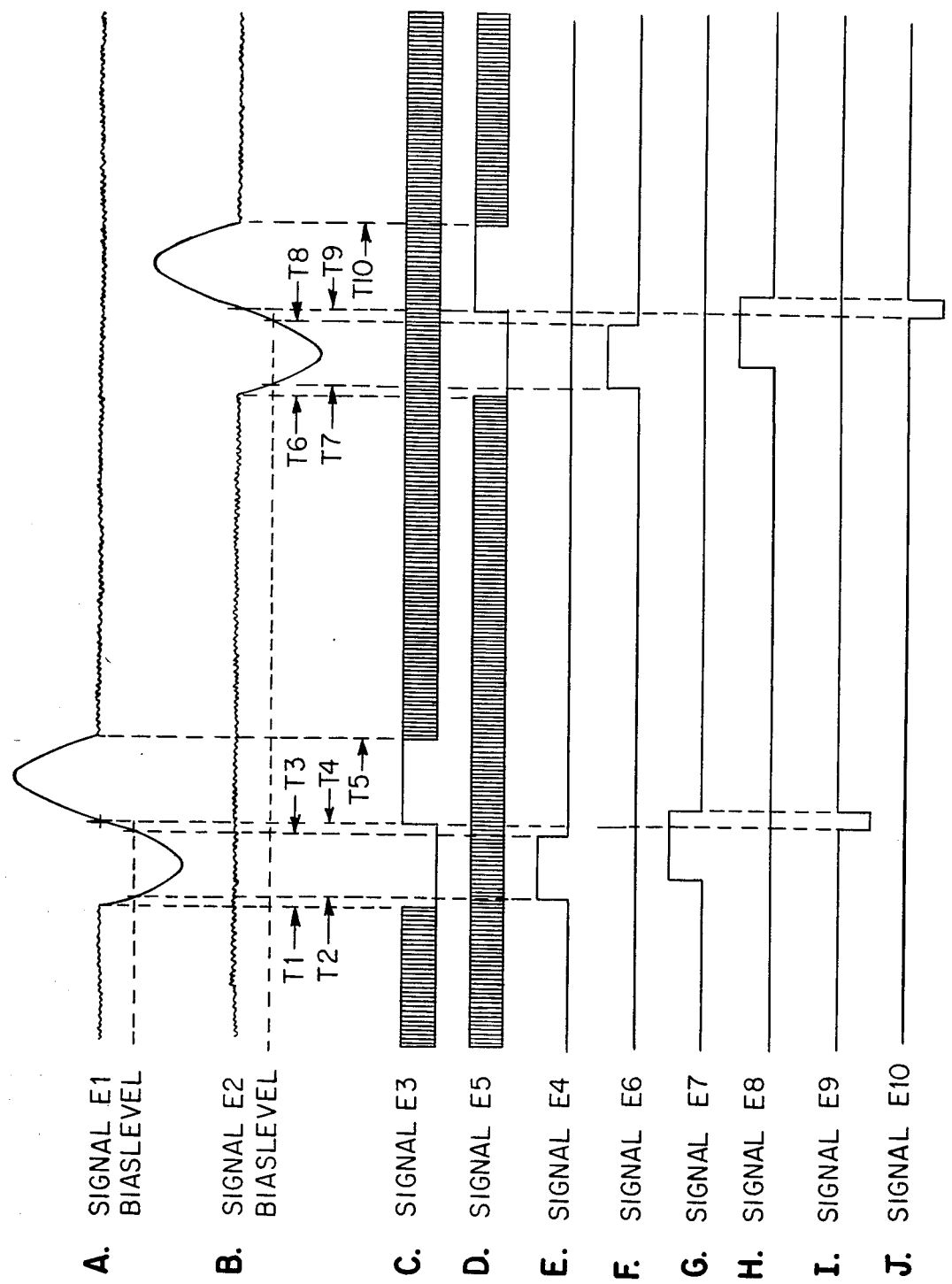

4,559,811

CONSISTOMETER

BACKGROUND OF THE INVENTION

Field of the Invention

The present invention relates to measuring devices for a refinery operation in the petroleum industry in general, and more particularly, to consistometers.

SUMMARY OF THE INVENTION

An improved consistometer which continuously measures the consistency of a stream of material from apparatus manufacturing the material includes a resilient blade rotated in the stream of material and which is rotated about an axis that is parallel to the direction of flow of the stream of material. A reference blade is rotated in synchronism with the resilient panel. A pair of detectors are arranged with the blade in the manner so that each detector detects the passage of a corresponding blade and provides a corresponding electrical signal. A circuit connected to the detectors provides a start pulse and a stop pulse in accordance with the signals from the detectors and not to noise. A clock provides timing pulses. A network connected to the start and stop pulse circuit and to the clock determines the consistency of the material in accordance with the start and stop pulses and the timing pulses.

The objects and advantages of the present invention will appear more fully hereinafter from a consideration of the detailed description which follows, taken together with the accompanying drawings, where one embodiment of the invention is illustrated by way of example. It is to be expressly understood, however, that the drawings are for illustration purposes only and are not to be construed as defining the limits of the invention.

DESCRIPTION OF THE DRAWINGS

FIG. 1 is a simplified block diagram of a consistometer constructed in accordance with the present invention.

FIGS. 2A through 2J are graphical representations of wave forms occurring during the operation of the consistometer shown in FIG. 1.

DESCRIPTION OF THE INVENTION

With reference to FIG. 1 a basic consistometer 5 such as that described and disclosed in U.S. Pat. No. 3,812,706, includes a detector sensor 42 and a reference sensor 43. In summary of the operation of the basic consistometer 5, detector sensor 42 detects the passage of a resilient blade rotating in a chamber through which a material, such as grease, continually flows. Axially aligned with the detector blade is a reference blade which is rotating in synchronism with the detector blade. Reference sensor 43 detects the passage of the reference blade. The basic concept of the consistometer is that as the blades rotate the consistency of the material will cause the detector blade to deflect in accordance with the consistency of the material and that the deflection can be measured electronically.

The present invention represents an improvement to consistometer 5 in the form of an improved noise gate and a more accurate method of determining the consistency using timing pulses. In this regard reference sensor 43 and detector 42 provides signals to amplifiers 101 and 102, respectively which in turn provides signals E1 and E2 respectively, as shown in FIGS. 2A and 2B respectively. It should be noted that as a blade passes its corresponding detector, the resulting signal from the detector will go negative from a substantially zero potential and then swing over to positive and return to its substantially zero potential. The fuzz shown along the substantially zero line of signals E1 and E2 in FIGS. 2A and 2B respectively represents noise. Signal E1 is provided to a "+" input of a comparator 106 and to "−" input of a comparator 107 while signal E2 is provided to a "+" input of a comparator 110 and to a "+" input of a comparator 111. A "−" input of comparator 106 is connected to ground 114. A "+" input of comparator 107 is connected to a biasing voltage potentiometer 118 through its wiper arm 119. As can been seen, one end of potentiometer 118 is receiving a negative voltage, while the other end of potentiometer 118 is connected to ground 114.

A "+" input of comparator 110 is connected to wiper arm 119 of potentiometer 118, while a "−" input of comparator 111 is connected to ground 114. Comparators 106, 107, 110 and 111 provides signals E3, E4, E6 and E5, respectively, as shown in FIGS. 2C, 2E, 2D and 2F, respectively. Signals E3 and E5 are provided to two input NAND gates 123 and 127, respectively. The other inputs of NAND gates 123 and 127 receive signals E7 and E8, respectively, shown in FIGS. 2G and 2H, respectively, from microcomputer means 130. NAND gates 123, 127 provides signals E9 and E10, respectively, to microcomputer means 130 which also receives timing pulses from timing pulse means 133. Signals E9, E10 are shown in FIGS. 2I and 2J, respectively.

In operation the reference blade in consistometer 5 will pass reference sensor 43 before the detector blade passes detector sensor 42 since the detector blade is being deflected by the material. As a result, as can be seen in FIGS. 2A and 2B, signal E1 will show the passage occurrence prior in time to signal E2. Until the reference blade passes reference sensor 43, the signal E1 from amplifier 101 is substantially at zero but noisy. What looks to be the shaded area in FIG. 2C of signal E3 represents noise spikes as the comparator 106 keeps going on and off in response to the noise going positive. However, as signal E1 starts to swing negative due to the passage of reference blade past reference sensor 43 it effectively causes comparator 106 to go into an off state at time T1. As signal E1 continues to go negative at time T2 it will be more negative than the bias level provided by potentiometer 118 so that comparator 107 in effect is turned on to provide signal E4 at a high logic level starting at time T2. Signal E1 continues going negative until it reaches a negative peak and then starts to swing positive. At time T3, signal E1 again passes the bias level so that the negative input of comparator 107 is approaching the ground potential, but since the "+" input of comparator 107 is receiving the bias voltage, comparator 107 is in effect turned off and signal E4 goes to a low logical level at time T3. When signal E4 went to a high logic level, it caused microcomputer means 130 to provide a high logic level pulse as signal E7. The delay between the start of signal E4 pulse and signal E7 pulse is controlled by microcomputer means 130.

As signal E1 continues it will pass through zero at time T4, causing comparator 106 to be turned on providing signal E3 at a high logic level. Signal E7 is at a high logic level. With both inputs receiving high logic level signals, NAND gate 123 povides a pulse signal E9 which is in essence the start of the counting of the timing pulses from timing pulse means 133. As signal E1 returns to its zero condition, signal E3 goes to its noisy state.

The timing continues until detector sensor 42 senses the passage of the detector blade and as a result signal E2 starts to follow the same pattern as hereinbefore described for signal E1, namely that times T6, T7, T8, T9 and T10 correspond to the times of T1 through T5 respectively. Similarly, E6 is provided in response to E2 the same as signal E4. Signal E8 is provided as was signal E7. The final result is a pulse signal E10 which stops the counting procedure internal in microcomputer means 130. Thus the count within microcomputer means 130 corresponds to the deflection of the detector blade. Microcomputer means 130 contains means (not shown) for displaying the count directly or may be programmed to display the consistency of the material in accordance with the count.

The consistometer as hereinbefore described is an improved noise rejection capability and an improved measuring method.

What is claimed is:

1. A consistometer for continuously measuring the consistency of a stream of material from apparatus manufacturing the material comprising:
   a rotatable resilient member located in said stream;
   means for rotating said member at a constant rate about an axis which is parallel to the direction of flow of said stream;
   a reference member;
   means for rotating the reference member in synchronism with the resilient member;
   resilient member sensing means spatially related to the resilient member for providing a resilient member signal in accordance with the movement of the resilient member;
   reference member sensing means spatially related to the reference member for providing a reference member signal in accordance with the movement of the reference member;
   means for providing a start pulse and a stop pulse in accordance with the resilient member signal and the reference member signal and not to noise, said start and stop pulse means includes:
   means for providing a biasing voltage,
   first noise signal means connected to the reference member sensing means and to the biasing means for providing a first noise indication signal representative of whether the resilient member signal is noise or indicative of the movement of the resilient member, and
   second noise signal means connected to the resilient member sensing means and to the biasing means for providing a second noise indication signal representative of whether the resilient member signal is noise or indicative of the movement of the resilient member;
   means for providing timing pulses;
   means connected to the start and stop pulse means and to the timing pulse means for determining the consistency of the material in accordance with the start and stop pulses and the timing pulses.

2. A consistometer as described in claim 1 in which the determining means receives both noise indication signals from the first and second noise signal means provides a first enabling pulse when the reference member noise indication signal is indicative that amplitude of the reference member signal is not noise and a second enabling pulse when the resilient member noise indication signal is indicative that the amplitude of the resilient member signal is not noise.

3. A consistometer as described in claim 2 in which the start/stop pulse means also includes:
   start pulse means for providing the start pulse in accordance with the reference signal member and the first enabling pulse, and
   stop pulse means for providing the stop pulse in accordance with the resilient member signal and the second enabling pulse.

4. A consistometer as described in claim 3 in which the start pulse means includes:
   first comparator means for comparing the reference member signal to ground and providing an output at a high logic level when the reference member signal is positive with respect to ground and at a low logic level when the reference member signal is not positive with respect to ground, and
   a first AND gate connected to the first comparator means and to the determining means which provides the start pulse in respone to the output from the first comparator means being at a high logic level and the occurrence of a first enabling pulse.

5. A consistometer as described in claim 4 in which the stop pulse means includes:
   second comparator means for comparing the resilient member signal with ground and providing an output at a high logic level when the resilient member signal is positive with respect to ground and at a low logic level when the resilient member signal is not positive with respect to ground, and
   a second NAND gate connected to the second comparator means and to the determining means for providing the stop pulse when the output from the second comparator means is at a high logic level and the second enabling pulse is provided by the determining means.

6. A consistometer as described in claim 5 in which the determining means determines the consistency of the material in accordance with the number of timing pulses that occur between the start and stop pulses.

* * * * *